(12) United States Patent
Zdravkovic et al.

(10) Patent No.: US 7,885,715 B2
(45) Date of Patent: Feb. 8, 2011

(54) METHODS FOR RESTORING AND MODULATING NEURAL ACTIVITY

(75) Inventors: Bojan Zdravkovic, Jersey City, NJ (US); Carlos Brathwaite, Brooklyn, NY (US); Walter Urbaniak, Peoria, IL (US)

(73) Assignee: Artis Nanomedica, Inc.

( * ) Notice: Subject to any disclaimer, the term of this patent is extended or adjusted under 35 U.S.C. 154(b) by 494 days.

(21) Appl. No.: 11/832,077

(22) Filed: Aug. 1, 2007

(65) Prior Publication Data

US 2008/0208304 A1  Aug. 28, 2008

(51) Int. Cl.
*A61N 1/05* (2006.01)
(52) U.S. Cl. .................................................. 607/118
(58) Field of Classification Search ............... 607/43, 607/48, 115–118
See application file for complete search history.

(56) References Cited

U.S. PATENT DOCUMENTS

| | | | | |
|---|---|---|---|---|
| 4,623,355 A | * | 11/1986 | Sawruk | 623/66.1 |
| 4,632,116 A | * | 12/1986 | Rosen et al. | 607/62 |
| 5,584,885 A | * | 12/1996 | Seckel | 623/11.11 |
| 6,185,452 B1 | * | 2/2001 | Schulman et al. | 604/20 |

* cited by examiner

*Primary Examiner*—Niketa I Patel
*Assistant Examiner*—Rex Holmes
(74) *Attorney, Agent, or Firm*—Jennifer Meredith, Esq.; Fariba Sirjani, Esq.; Meredith & Keyhani, PLLC

(57) ABSTRACT

A method of reviving and maintaining a severed nerve tissue or a bundle of nerves of a body comprising the steps of: providing a housing for conducting and modulating neural response having a first end, a second end and a cavity, wherein the cavity is interposed between the first end and second end and the first end of said housing has a plurality of openings and the second end of the housing has a plurality of openings; providing at least one conductor in communication with at least one of the first end of the housing and the second end of the housing, wherein each of the conductors are adapted to attach to at least one first nerve ending; and transporting fluids between the first nerve ending and the second nerve ending.

5 Claims, 7 Drawing Sheets

Figure 11
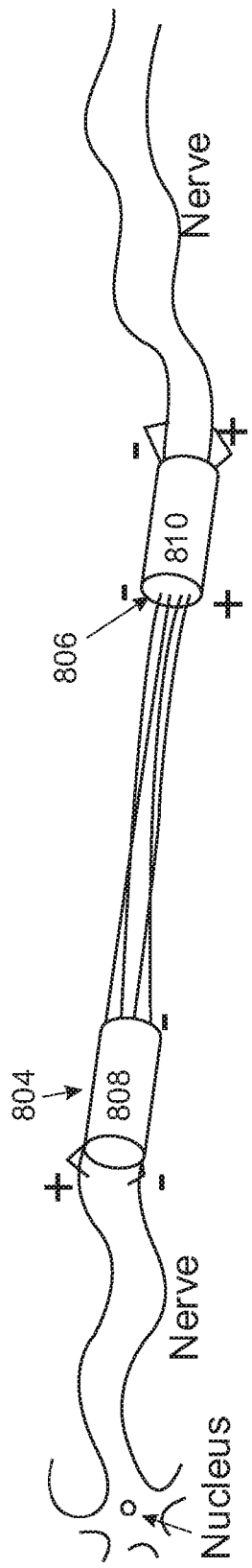
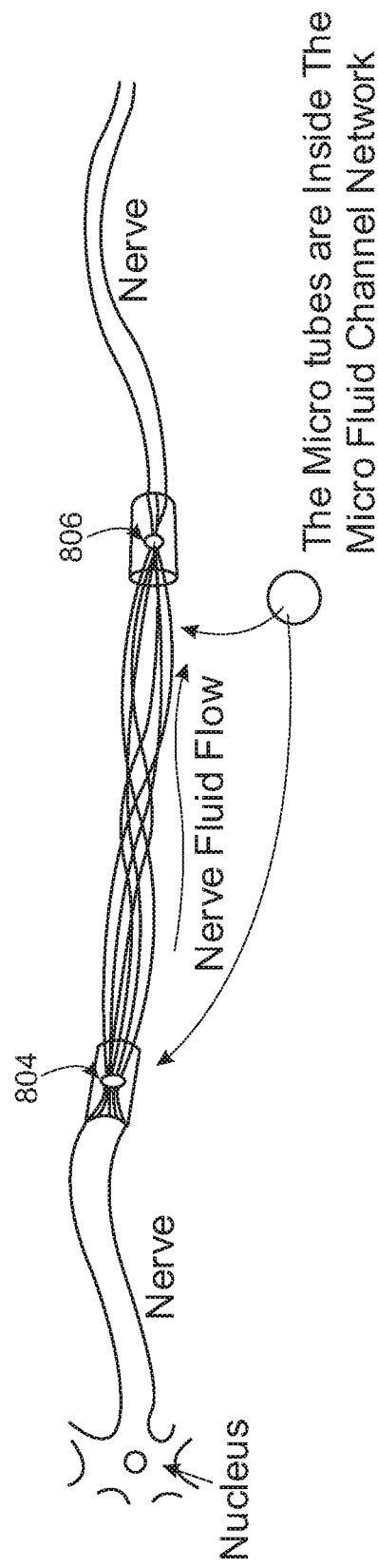

METHODS FOR RESTORING AND MODULATING NEURAL ACTIVITY

This application is related to and claims priority to Ser. No. 10/840,903 as filed on May 8, 2004.

BACKGROUND OF THE INVENTION

The present invention relates to several art areas. In one aspect, the invention relates to the recent achievements in building small-scale, micro and nano-size, electromechanical apparatuses and computing components. According to another aspect, the main application of the invention is to facilitate restoring the functionality of an impaired human nervous system. In still other aspect, the invention may modulate the activity of the nervous system.

The evolving area of micro-electromechanical systems ("MEMS") makes it possible to assemble complex functioning mechanical devices on a level which may not even be recognized by unaided human eye. The dominant portion of new developments in the area of MEMS is geared toward the computer industry, such as development of micro- and nano-scale non-volatile memory, batteries, magnets, capacitors, and motors.

It is generally accepted that the human nervous system consists of the brain, the spinal cord and nerves. A nerve cell is an elementary building block of the nervous system. A nerve cell generally has three identifiable regions: a cell body, or soma, short outgrowths, or dendrites, and a long outgrowth, or an axon. There are a great variety of nerve cells characterized primarily by the difference in the dimension of axon part and the localization of a cell body.

Some nerve cells have all theirs parts located in a single place such as the brain. Other cells have their axons running substantial distances. For instance, the axon may run from the brain along the entire length of a spinal cord. The axon is primarily responsible for conducting signals from one nerve cell to another or for conducting stimulus to and from other organs. Further, the nerve cells whose axons run from and to the brain along the spinal cord interact with other nerve cells, including peripheral nerves, whose cell bodies are primarily located in the so called spinal roots or dorsal ganglia. The nervous system also makes sure that organs and tissues, such as muscles, function properly.

The peripheral nerves are primarily divided into three main groups: (1) sensory, or afferent, (2) motor, or efferent, and (3) nerves of the autonomic system. Further, the nerves in each group are generally subdivided based on the diameter of axon, or a conducting fiber.

An inactive axon usually has a small negative potential, a resting potential, inside the cell due to distribution of ions inside and outside of the axon. An a nerve impulse starts generally when a nerve cell experiences an increased influx of ions, usually sodium ions which leads to depolarization of inner cell membrane of an axon for a short period of time. The depolarization at a particular place in the axon, if it is strong enough, would propagate itself into neighboring regions, generally, by diffusion of sodium ions. Immediately, the increased influx of sodium ions provokes the increased outflow of potassium ions at the place to where the initial impulse came in. In a short period, at the initial place of excitation the system returns to equilibrium, while the depolarization, i.e. the impulse continues to travel along the axon.

Some axons, generally referred to as white matter, stretching for substantial distances, have special shielding material around them which is interrupted by small portions of a naked nerve cell. In such axons, it is believed that the depolarization can only occur at the naked sections allowing the impulse to travel long distances without substantial decrease in its depolarizing ability. Unfortunately, many diseases and injuries may lead to partial or complete severance of the neural conductive pathways, i.e. axons.

For instance, one such injury is a spinal cord injury which could result when a person experiences a catastrophic fall, such as being thrown from a horse or being in a severe car accident. Depending on the area of the spinal cord, the injury may even lead to total paralysis of hands and legs, known as quadriplegic condition. Many thousands of spinal cord injuries occur in the United States each year. It is estimated that it generally costs over four billion dollars to care for people with spinal cord injuries.

There have been many attempts to address the problem of a severed nerve cell. Some attempts concentrate on different ways to secure the severed ends together. Another attempt, in addition to securing both ends of an axon, propose using electro-charged surfaces or surfaces covered with different chemical and biological compositions to stimulate the regeneration. Still other attempts propose uniting the severed ends and using microelectrodes to stimulate the neural endings from an outside source.

While the proposed solutions may provide for a way to hold ends of a severed nerve, they do not overcome a pivotal problem of supporting the propagation of action potential from a primary end to another. Further, many proposed solutions add a substantial outside structure over a severed nerve which may exert negative pressure on the neighboring nerves and other tissue.

U.S. Pat. No. 4,308,868, entitled "Implantable electrical device" discloses a fully implantable and self-contained device composed of a flexible electrode array 10 for surrounding damaged nerves and a signal generator 12 for driving the electrode array with periodic electrical impulses of nanoampere magnitude to induce regeneration of the damaged nerves.

U.S. Pat. No. 5,314,458, entitled "Single channel microstimulator" discloses an implantable microstimulator system employs a miniature ferrite-cored coil contained with an hermetically sealed housing to receive control signals and operating power from an RF telemetry system. The tiny coil receives the electromagnetic energy which is transmitted from a non-implantable transmitter which generates a code-modulated carrier. Demodulator circuitry in the implantable microcircuit is employed to extract the control information, while applying the electromagnetic energy to power the electronic circuitry therein and charge a capacitor which will provide the electrical stimulation to the living being. The electrical stimulation is delivered by a stimulating electrode which has a waffle-like configuration whereby a plurality of iridium oxide electrode pads, coupled in parallel, so as to be characterized by a long effective edge distance, transfer the stimulating charge. The electrical components of the implantable microstimulator are contained within an hermetically sealed housing formed of a glass capsule which is electrostatically bonded to a silicon substrate.

U.S. Pat. No. 5,030,225, entitled "Electrically-charged nerve guidance channels" discloses a medical device is disclosed for use in regenerating a severed nerve. The device includes an implantable, tubular, electrically-charged membrane having openings adapted to receive the ends of the severed nerve and a lumen having a diameter ranging from about 0.5 millimeters to about 2.0 centimeters to permit regeneration of the nerve therethrough. The membrane is fabricated such that an electric charge is exhibited at the inner membrane surface to stimulate regeneration by axonal sprouting and process extension. Also disclosed are methods for repairing a severed nerve and for preparing a medical device for use in regeneration of a severed nerve.

U.S. Pat. No. 4,878,913, entitled "Devices for neural signal transmission" discloses devices and methods for transmitting neural signals from a proximal stump of a transected nerve to a prosthetic apparatus are disclosed employing microelectrodes, preferably conductive fiber networks, capable of sensing electrical signals from a nerve and transmitting such signals to a prosthetic apparatus; and a semipermeable guidance channel disposed about the microelectrodes. The channels include an opening adapted to receive the proximal stump of a transected nerve, such that the channel promotes the growth of the stump and the formation of an electrical connection between the transected nerve and the microelectrode.

U.S. Pat. No. 6,235,041, entitled "Medical device for treatment of a gap or defect in the central nerve system" discloses a medical device (1) of a biocompatible material for use in the treatment of a gap or defect in the central nervous system, which device has a proximal end (5) and a distal end (6) comprising openings (7). The device is adapted to enable connection of nerve fibers of gray and white matter between the proximal end (5) and distal end (6) thereof in predetermined openings (7). The device is of a substantially cylindrical form, or a substantially flat or plate like form and is made of plastic. The openings (7) in at least one end (5, 6) bear distinctively different indicia thereby to indicate whether nerve fibers of gray matter or nerve fibers of white matter are to be inserted therein.

U.S. Pat. No. 5,354,305, entitled "Nerve repair device" discloses a nerve repair device which includes a resilient, elongated implant, and transverse pins for retaining the implant fixedly within the ends of the severed nerve. A sharp tip extends longitudinally from at least one end of the elongated implant, and aids in the insertion of the implant longitudinally through the ends of the severed nerve between the fascicle bundles. The severed ends are retained in close approximation for reconnection.

U.S. Pat. No. 4,778,467, entitled "Prostheses and methods for promoting nerve regeneration and for inhibiting the formation of neuromas" is directed to prosthesis and methods for promoting nerve regeneration. The proximal and distal ends of a severed nerve are brought into close proximity and are enclosed by a tubular prosthesis. In one preferred embodiment, a epineurial or endoneurial monosuture is used to hold the nerve ends in close proximity. A tight seal is formed between the prosthesis and the injured nerve so as to isolate the injured nerve within the prosthesis from the rest of the body of the host. Additionally, in one preferred embodiment, nerve grafts may be incorporated into the prosthesis and nerve regeneration promoting substances may be incorporated within the nerve graft to further enhance nerve regeneration. In another preferred embodiment, a prosthesis is coated with a material which is slippery with relation to the surrounding body tissue and the prosthesis is formed of or coated with a material around the inside of the prosthesis which will substantially adhere to the severed nerve ends so as to prevent substantial movement of the severed nerve ends within the prosthesis. In yet another preferred embodiment, such an outside coating around the prosthesis terminates in two longitudinal flaps which serve to form a fluid-tight seal along the tubular prosthesis. In still another preferred embodiment, the ends of the prosthesis overlap and are formed so as to bias against each other in a spiral tube configuration, thereby providing for firm closure of the prosthesis around a variety of sizes of injured nerves. Also disclosed are various devices and methods for inhibiting the formation of neuromas, such as an open-ended tube or a neuroma-inhibition device formed as a cap member having a reservoir formed therein.

U.S. Pat. No. 4,306,561, entitled "Holding apparatus for repairing severed nerves and method of using the same" discloses circumferentially embracing both the proximal and distal portions of a severed nerve at positions removed from the severed ends and controllably moving the severed portions into abutting, juxtaposed contacting relationship, the reattachment and repair of severed nerves is achieved. Preferably, both portions of the severed nerve are embraced within a holding member which incorporates nerve securing means at the desired location. In addition, the preferred nerve holding member incorporates nerve cooling components, electrical pulse stimulation means for directing a pulse from the proximal portion towards the distal portion, and temperature sensing components for monitoring the temperature of the nerve.

U.S. Pat. No. 5,038,781, entitled "Multi-electrode neurological stimulation apparatus" discloses an implantable system for Functional Electro-Stimulation (FES), which includes an environmentally sealed implant case and a nerve cuff for attaching to the nerve. A plurality of leads connect the nerve cuffs to the case. The implant case provides redundant seals for entrance of the leads in a double wall/double environmental seal to provide long term sealing reliability for the case. Inside the case, the wires in each lead attach to connectors, which establish contact with an enclosed master circuitry case. The connectors allow the leads to be individually removed and replaced, thereby providing a maintainable system. At the other end of the leads is attached the nerve cuff. Each nerve cuff has a hollow, gapped cylindrical shape, and includes electrodes on its inner surface. The cuff is deformable to allow placement around the nerve, holding the electrodes in electrical contact therewith. In other embodiments of the invention, the nerve cuff includes a micro circuit which is capable of demultiplexing stimulation signals from a single pair of wires in the lead to drive multiple electrodes. These embodiments reduce the number of wires needed in each lead to facilitate the stimulation of a large number of nerves with a single implant.

U.S. Pat. No. 5,300,096, entitled "Electromyographic treatment device" discloses an electrical muscle stimulator converts electromyographic (EMG) signals to digital words for analysis and display by a computer program. The therapist selects a variety of different parameters appropriate for the individual patient, and instructs the device to initiate stimulating signals on command, or upon detection of a suitable EMG signal from the patient. The device that converts digital words representing the selected parameters into complex, bipolar therapeutic pulses. The device can digitally model a wide variety of wave forms and graphically assist the therapist in developing and shaping various wave pulse trains.

U.S. Pat. No. 5,041,974, entitled "Multichannel stimulator for tuned stimulation" discloses a multichannel stimulator device having a host user interface circuit for enabling a user to select a channel and easily create and display a stimulus wave signal for the selected channel and generate a data signal specifying the channel and stimulus wave signal. The stimulator also includes a master circuit for receiving the data signal and directing it to the specified channel as a wave building instruction signal. A slave circuit associated with the channel specified receives the wave building signal and responds by generating a corresponding low power stimulus wave signal in the channel specified. Then an output circuit coupled to the slave circuit electrically isolates the low power stimulus wave signal from other channels, amplifying and converting it to a corresponding high fidelity current stimulus wave signal.

U.S. Patent Application No. 20040024439 entitled "Nerve cuff electrode" discloses a nerve electrode system for stimulating and/or monitoring at least one nerve fascicle in a trunk nerve comprising at least one internal electrode and at least one external electrode. The invention also relates to a multi-polar nerve cuff, a method of installing a nerve electrode system or a multi-polar nerve cuff and finally the invention relates to uses of the nerve electrode system or the multi-polar nerve cuff.

U.S. Patent Application No. 20020120309, entitled "System and method for providing recovery from muscle denervation". Recovery from peripheral nerve and nerve plexus injuries is usually slow and incomplete because the regenerating motor axons often head erroneously toward sensory receptors rather than muscle fibers and because the target muscles atrophy while waiting for the slow process of reinnervation. Research has suggested that electrical stimulation with different waveforms and temporal patterns at different times during the regeneration process might improve the clinical outcome through various mechanisms, but a practical means to deliver such stimulation has been lacking. This invention teaches the use of miniature electrical stimulators that can be implanted alongside the injured nerve(s) at the time of surgical repair and that can be powered and controlled by transmission of radiofrequency energy from outside the body so as to provide a variety of electrical stimuli at different times during the recovery process.

U.S. Patent Application No. 20030176876, entitled "Multi-channel bioresorbable nerve regeneration conduit and process for preparing the same" discloses a multi-channel bioresorbable nerve regeneration conduit and a process for preparing the conduit. The multi-channel bioresorbable nerve regeneration conduit includes a hollow round tube of a porous bioresorbable polymer and a multi-channel filler in the round tube. The multi-channel filler is a porous bioresorbable polymer film with an uneven surface and is single layer, multiple layer, in a folded form, or wound into a spiral shape.

U.S. Patent Application No. 20030153965, entitled "Electrically conducting nanocomposite materials for biomedical applications" discloses exposing osteoblasts on an electrically conducting nanocomposite, which may be an orthopaedic/dental implant, to electrical stimulation enhances osteoblast proliferation thereon. The electrically conducting nanoscale material includes an electrically conducting nanoscale material and a biocompatible polymer and/or a biocompatible ceramic; carbon nanotubes may be used as the electrically conducting nanoscale material.

U.S. Patent Application No. 20010031974, entitled "Neural regeneration conduit" discloses a neural regeneration conduit employing spiral geometry is disclosed. The spiral geometry is produced by rolling a flat sheet into a cylinder. The conduit can contain a multiplicity of functional layers lining the lumen of the conduit, including a confluent layer of adherent Schwann cells. The conduit can produce a neurotrophic agent concentration gradient by virtue of neurotrophic agent-laden microspheres arranged in a nonuniform pattern and embedded in a polymer hydrogen layer lining the lumen of the conduit.

U.S. Patent Application No. 20020193858 entitled "Miniature implantable connectors" discloses methods of making electrical connections in living tissue between an electrically conductive wire and an implantable miniature device. The device may either stimulate muscles or nerves in the body or detect signals and transmit these signals outside the body or transmit the signals for use at another location within the body. The device is comprised of an electrically insulating or electrically conductive case with at least one electrode for transmitting electrical signals. The electrodes and the wire-electrode connections are protected from the aggressive environment within the body to avoid corrosion of the electrode and to avoid damage to the living tissue surrounding the device.

U.S. Patent Application No. 20040015205 entitled "Implantable microstimulators with programmable multi-electrode configuration and uses thereof" discloses miniature implantable stimulators (i.e., microstimulators) with programmably configurable electrodes allow, among other things, steering of the electric fields created. In addition, the microstimulators are capable of producing unidirectionally propagating action potentials (UPAPs).

U.S. Patent Application No. 20040015204 entitled "Implantable microstimulators and methods for unidirectional propagation of action potentials" discloses miniature implantable stimulators (i.e., microstimulators) are capable of producing unidirectionally propagating action potentials (UPAPs). The methods and configurations described may, for instance, arrest action potentials traveling in one direction, arrest action potentials of small diameters nerve fibers, arrest action potentials of large diameter nerve fibers. These methods and systems may limit side effects of bidirectional and/or less targeted stimulation.

U.S. Patent Application No. 20030181956 entitled "Multi-purpose FES system" discloses a multi-purpose FES system which includes a multi-function, implantable stimulator for stimulating different sites in a patient's body. The stimulator includes a control unit and a receiving device. The stimulator further has a plurality of bundles of electric leads connected to the control unit, each lead terminating in at least one electrode to provide a plurality of discrete groups of electrodes associated with each site. Each group of electrodes is operable to stimulate its associated site in the patient's body, under the action of stimulation signals from the control unit, the control unit receiving signals from the receiving device. A transmitter is arranged externally of the patient's body for supplying signals transcutaneously to the receiving device of the stimulator. A controller is in communication with the transmitter via a communications interface unit.

U.S. Patent Application No. 20030171785 entitled "Distributed functional electrical stimulation system" discloses a multi-purpose, functional electrical stimulation (FES) system includes an implantable stimulator unit for stimulating a plurality of different sites in a patient's body. A transmitter is arranged externally of the patient's body for supplying signals transcutaneously to the stimulator unit. A controller is in communication with the transmitter. At least one implantable switching node has an input terminal in electrical communication with the stimulator unit and a plurality of output terminals to each of which one of a further switching node and a stimulating element is connected. The switching node including addressing circuitry for switching at least one output terminal into electrical connection with the input terminal of the switching node in response to a control signal received from the controller via the stimulator unit.

U.S. Patent Application No. 20030149457 entitled "Responsive electrical stimulation for movement disorders" discloses an implantable neurostimulator system for treating movement disorders includes a sensor, a detection subsystem capable of identifying episodes of a movement disorder by analyzing a signal received from the sensor, and a therapy subsystem capable of applying therapeutic electrical stimulation to treat the movement disorder. The system treats movement disorders by detecting physiological conditions characteristic of an episode of symptoms of the movement disorder and selectively initiating therapy when such conditions are detected.

U.S. Patent Application No. 20030144710 entitled "Method and implantable systems for neural sensing and nerve stimulation" discloses an invention which relates to methods and apparatuses for the detection of neural or muscular activity, analysis of the signals and the subsequent stimulating of neural or muscular tissue based thereon. According to a first aspect of the invention an apparatus for producing a muscular action is provided, comprising a combined sensing and stimulation electrode device comprising at least one neurosense electrode means capable of sensing a nerve signal from a peripheral nerve and at least one stimulation electrode means capable of stimulating a peripheral motor nerve fibre, means for receiving and processing the sensed neurosignals to identify a signal indicative of a specific action, especially a component of the gait performed by the patient and for producing a control signal in response thereto, and means for operating the at least one stimulation electrode means in response to the control signal to produce a stimulation of a peripheral motor nerve fibre.

U.S. Patent Application No. 20010000187 entitled, "Functional neuromuscular stimulation system" discloses an input command controller (A) provides logic function selection signals and proportional signals. The signals are generated by movement of a ball member (12) and socket member (14) relative to two orthogonal axes. When the joystick is implanted, a transmitter (50) transmits the signals to a patient carried unit (B). The patient carried unit includes an amplitude modulation algorithm such as a look-up table (124), a pulse width modulation algorithm (132), and an interpulse interval modulation algorithm (128). The algorithms derive corresponding stimulus pulse train parameters from the proportional signal which parameters are transmitted to an implanted unit (D). The implanted unit has a power supply (302) that is powered by the carrier frequency of the transmitted signal and stimulation pulse train parameter decoders (314, 316, 318). An output unit (320) assembles pulse trains with the decoded parameters for application to implanted electrodes (E). A laboratory system (C) is periodically connected with the patient carried unit to measure for changes in patient performance and response and reprogram the algorithm accordingly. The laboratory system also performs initial examination, set up, and other functions.

U.S. Patent Application No. 20030208246 entitled "Electrostimulation system with electromyographic and visual biofeedback" provided an electrostimulation system with electromyographic and visual biofeed-back for sensing electromyographic impulses and facilitating muscular activity. The electrostimulation system comprises stimulator that is adapted to generate an electric impulse and at least one pair of electrodes adapted to transmit the electric impulse or to receive electromyographic impulses. The system further comprises an amplifier electrically communicating with the pair of electrodes, the amplifier is adapted to amplify the received electromyographic impulses and a filtering unit electrically communicating with the amplifier and is adapted to remove artifacts from the received electromyographic impulse. A commutation block is electrically communicating with the pair of electrodes and is adapted to alternately transfer the electromyographic impulses to the amplifier or to transfer the generated electric impulse from the stimulator. A display for displaying the received electromyographic impulses and a predetermined threshold value is also provided as well as a control unit that is adapted to receive the electromyographic impulses from the amplifier and to activate the stimulator in a predetermined manner. The stimulator incorporated in the present invention is triggered to transmit impulses to the rehabilitated muscle when the electromyographic impulse substantially equals or exceeds the predetermined threshold value.

One type of prior art solution attempts to deal directly with the aftermath of a spinal cord injury by trying to somehow repair the severed nerve cells. Another type of prior art solution concentrates on addressing the consequences of a spinal cord injury such as the inability of an injured person to control bodily functions below the injured area. Such solutions propose external micro-stimulators which are placed around or embedded into one or several peripheral nerves and which stimulate those nerves in accordance with a necessary regime.

Most solutions consist of a conducting plate or a plurality of micro-electrodes. Some solutions propose a system in which micro-stimulating an implant may have power generating and storing ability, an ability to communicate, and an ability to affect the propagation of action potential in a nerve.

However, implant systems have certain disadvantages. One disadvantage is an implant imposes a substantial outside structure over a nerve. The nerve may exert negative pressure on the neighboring nerves and other tissue. Another disadvantage is that such implant is unable to fully function autonomously because of its inability to convert the electrochemical energy of an action potential into an electrical power. Still other disadvantage is that such a system lacks the functionality to read the nerve cell own action potentials and to produce or modulate the action potentials based on these readings without reserving to any external communications.

SUMMARY OF THE INVENTION

The present invention provides a method of reviving and maintaining a severed nerve tissue or bundle of nerves. The method may use a device and a neural bridge, for connecting endings of nerve cells and conducting neural signals. The device may have a housing for conducting and modulating a neural response, wherein the housing may have a first end, a second end and a cavity. In some aspects of the invention, the housing is made of electrostatic material. The first end of the housing has a plurality of openings, and the second end of the housing has a plurality of openings as well. In some aspects of the invention, the openings have the same size and shape. In some other aspects of the invention, the openings have different size and shape. There may be at least one microfluid channel facilitating movement of cell material from a primary end of a severed nerve to the other. In still further aspects of invention, there is at least one ion-guiding channel connected to one of the openings on the first side of the housing. The device further comprises at least one rotating mechanism, wherein the rotating mechanism rotates within the cavity. In some aspects of the invention, the rotating mechanism has needle-like protrusions set at certain angle which carry the same electrical charge as ions entering the cavity through the ion-guiding channels. The device still comprises at least one generator mechanism also positioned within the cavity of the housing and connected to the rotating mechanism. The generator mechanism generates electric current upon rotation of the rotating mechanism. In some aspects of the invention the generator mechanism produces at least 7 mV-60 mV. The device also comprises a plurality of conductors for collecting current from the generator mechanism, wherein the plurality of conductors attach to a nerve ending. In some aspects of the invention, the conductors are made out of polyacetylene. The device further comprises various MEMS device for sensing and modulating neural signals and responses.

According to another embodiment of the invention, a method of reviving and maintaining a severed nerve tissue or a bundle of nerves of a body, said method comprising the steps of: providing a housing for conducting and modulating neural response, the housing having a first end, a second end and a cavity, wherein said cavity is interposed between the first end and the second end and the first end of the housing has a plurality of openings and the second end of the housing has a plurality of openings; providing at least one conductor in communication with at least one of the first end and the second end for collecting current from the generator mechanism, wherein each of the plurality of conductors are adapted to attach to at least one first nerve ending and the generator mechanism; and transporting fluids between the first nerve ending and the second nerve ending.

According to another embodiment of the invention, a method of reviving and maintaining a severed nerve tissue or a bundle of nerves of a body is provided, the method comprising the steps of: providing a device for connecting endings of nerve cells and conducting neural signals, the device comprising: a housing for conducting and modulating neural response, the housing having a first end, a second end and a cavity, wherein the cavity is interposed between the first end and the second end and the first end of the housing has a plurality of openings and the second end of the housing has a plurality of openings; at least one generator mechanism; and a plurality of conductors for collecting current from the generator mechanism, wherein each of the plurality of conductors are adapted to attach to a nerve ending and the generator mechanism; at least one ion-guiding channel, wherein at least one of the openings on the first end of the housing is connected to one of the at least one ion-guiding channel; and transporting fluids between the first nerve ending and the second nerve ending.

According to still other aspects of the invention, the invention includes a method for modulating nerve signals or responses. The various types of neural bridge devices carrying some or all of the MEMS devices are secured between the first end of a severed nerve and the second end of a severed nerve. The desired signals are communicated to the devices by any suitable means. The neural bridge device modifies receiving nerve signals in accordance with the desired signals communicated to these devices. In some aspects of the invention, the devices communicate the signals away from the devices by any suitable means. In still other aspects of the invention, the devices communicate the desired signals among each other in synchronous or asynchronous manner. In still further aspects of the invention, the devices modify nerve responses outside a particular nerve cell containing one or many neural bridge devices.

BRIEF DESCRIPTION OF THE DRAWINGS

FIG. 11 is a diagram according to one aspect of the present invention.

DETAILED DESCRIPTION OF THE INVENTION

The present invention is capable of many different embodiments, and modifications in various respects, all without departing from the present invention. Accordingly, the drawings and description are to be considered as illustrative in nature, and not as restrictive.

The present invention may be employed for the treatment of various medical conditions in which the continuity of nerve cells, for example the axon part of a cell, is destroyed due to a disease or an injury. One example of such an injury may be a spinal cord injury. In this implementation, the method may consist of providing a housing device which may be implanted into a place of an injury by connecting the first end of the device to a primary end of a severed axon and connecting the second end of the device to a secondary end of the severed axon. In this respect, the device serves as a bridge between two severed ends. The device may use the cell's condition of active potential on a primary end of the device, generate electrical power, and use this electrical power to initiate action potentials on a secondary end of the device. Fluids may be transported between the first nerve ending and the second nerve ending.

One advantage of the present invention is that it provides a device that does not impose any substantial outside structure over a nerve which may exert negative pressure on the neighboring nerves and other tissue. Another advantage is that the device is able to function fully autonomously because of its ability to convert the electrochemical energy of an action potential into an electrical power. Still other advantage is that the invention is able to read the nerve cells own action potentials and produce or modulate the action potentials based on these readings without reserving to any external communications.

Figure 1:
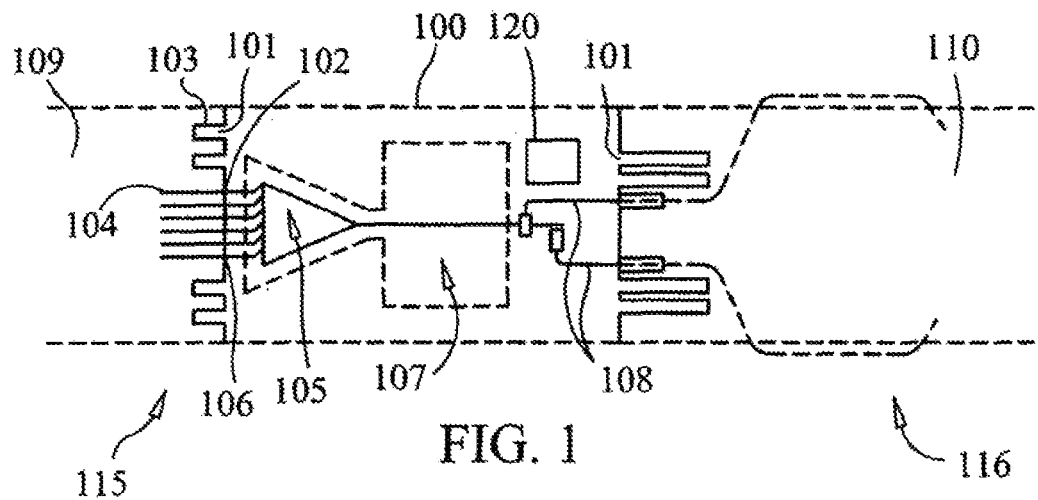
FIG. 1 is a diagram according to one aspect of the present invention.

The invention will be now illustrated in reference to the accompanying drawings. FIG. 1 depicts a block diagram according to a preferred embodiment of the present invention. In some preferred embodiments and methods of operation, the neural bridge device made in accordance with the invention, FIG. 1, may incorporate a housing 100 having a first end 115, a second end 116 and a cavity. The diameter of the housing 100 may vary from approximately 1 μm to approximately 1 cm, depending on the type of nerve cells in which said device may be implanted. The length of the device may vary depending on the extensiveness of a particular medical condition. In some embodiments, the length of the device varies from approximately 2 μm to approximately 1 cm. In some other embodiments, the housing 100 may be made from any electrostatic plastic material such as cellophane or a more rigorous material like a diamond.

The first end 115 and second end 116 of the housing 100 may have at least two types of openings. In some embodiments, there are at least two openings of each type. In some other embodiments, the openings on the first end 115 of the housing 100 may be of the same size and shape, and the openings on the second end 116 of the housing 100 may be of the same size and shape.

In some preferred embodiments, the openings may vary in diameter. The openings of first type 101 may have a larger diameter than the openings of the second type 102. In still other embodiments, the openings of the second type 102 may be present only on first end 115 of the housing 100. The openings of the first type 101 may have a larger diameter and may serve for movement of cell material through the device which may permit to restore the anterograde and retrograde exchange of cell material between the severed parts of a nerve.

The openings of the first type 101 on the first end 115 of the housing 100 and the opening of the first type 101 on the second end 116 of the housing 100 may merge or may be connected to hollow tubular extensions 103 which may have the same diameter as the diameter of the openings of the first type 101. In some preferred embodiments, the openings of the first type 101 on the first end 115 of the housing 100 may be connected with the opening of the first type 101 located on the second side 116 of the housing 100 by a connective tube or a cavity of some other shape. Such unity of hollow tubular extension and the opening of the first type 101 of the first end 115 of the housing 100 with a connective tube and the opening of the first type 101 of the second end 116 of the housing 100 may create a single cavity, which may be called a microfluid channel. In some embodiments, the microfluid channel may be made as a single form having a hollow inside, for example it may be in a form of a tube, which may go through entire device. The length of the microfluid channel may vary from 1 µm to 5 cm. The microfluid channel may allow for unimpeded traveling of cell material from the first end 115 of the severed axon to the second end 116 of the severed axon.

The openings of the second type 102 on the first end 115 of the housing 100 may have a smaller diameter and may serve to direct ions such as sodium ions to enter the cavity of the housing 100. The ions may enter a nerve cell at increased numbers during the depolarization stage of an action potential. The openings of the second type 102 may merge or may be connected to some hollow tubular extension 104, for example it may be a tube. A unity of the opening of the second type 102 and the hollow tubular extension 104 may be called an ion-guiding channel. In some embodiments, the ion-guiding channel may have the same diameter as the diameter of the openings of the second type 102.

The invention may further incorporate at least one rotating mechanism 105 positioned within (or outside in another embodiment) the cavity of the housing 100. The rotating mechanism 105 may rotate within the cavity of the housing 100. The rotating mechanism 105 may be a turbine, shaped like a cone, positioned such that the sharpest end may look inside the housing 100. The rotating mechanism 105 may have needle-like protrusions 106 which may be referred as micro-terminals. The micro-terminals may carry an electric charge. The micro-terminals may be positioned to face the second type 102 openings, or ion-guiding channels on the first end 115 of the housing 100.

The needle-like protrusions 106, or micro-terminals, may be set at an angle of approximately thirty to approximately sixty degrees relatively to the plane of the ion-guiding channels linked to the openings of the second type 102. In some preferred embodiments, the micro-terminals may be positioned at approximately forty-five degrees relatively to the plane of the ion-guiding channels linked to the openings of the second type 102. The needle-like protrusions 106, or micro-terminals, may have the same charge as the ions entering the housing 100 through the ion-guiding channels.

In some preferred embodiments, the micro-terminals may carry positive charge. During an action potential, sodium ions, which may enter the cell during the depolarization stage of the action potential, may be directed by the ion-guiding channels toward the micro-terminals of the rotating mechanism 105. Since sodium ions and the micro-terminals have the same charge, the micro-terminals may be repelled away from the ion-guiding channels. The process of repulsion may displace the rotating mechanism 105 and bring about the rotation of the rotating mechanism 105.

The invention may further incorporate at least one generator mechanism 107 positioned within the cavity of the housing 100 and connected to the rotating mechanism 105. For example, when rotating mechanism 105 may have shape of a cone, the generator mechanism 107 may be connected to the sharpest end. In some preferred embodiments, the generator mechanism 107 may represent a cluster of conducting wires rotating between the poles of a magnet or an electromechanical motor such as a dynamo. The device 100 may be self-powered. The term self-powered is intended to include many forms of power generation including dynamos, neural activity, magnetic, batteries or any combination thereof. It is also envisioned that a power source external to the body may be utilize in accordance with the present invention. By way of example, a bracelet containing a battery may communicate with the device and act as a generator or power generation means.

The displacement of the rotating mechanism 105 upon influx, or entry, of sodium ions through the ion-guiding channels linked to the openings of the second type 102 may result in the rotation of the rotating mechanism 105 which may result in movement of some part of the generator mechanism 107 such as conducting wires around a magnet if the generator mechanism 107 may consist of conducting wires and a magnet or a rotor in an electromechanical motor if the generator mechanism 107 may consist of an electromotor.

The rotation of a part of the generator mechanism 107 such as conducting wires or rotor may result in changes in magnetic field within the generator mechanism 107. In accordance with the Faraday laws, these changes may produce current within the generator mechanism 107, for example in conducting wires or in a stator of an electromechanical motor. In some embodiments, the generator mechanism 107 may produce electric potential from at least approximately 7 mV to approximately 60 mV.

The invention may further incorporate a plurality of conductors 108 for collecting and moving current from the generator mechanism 107. In some embodiments, there may be at least two conductors 108. Some of the conductors 108 may be connected to the cathode terminals of the generator mechanism 107 and some of the conductors 108 may be connected to the anode terminals of the generator mechanism 107.

A single conductor may be a piece of a wire from any conducting material such as copper. In some other preferred embodiments, the conductors 108 may be made out of polyacytelene. In some still other preferred embodiments, the conductors 108 may be made in a shape of a tube of micro- or nano size. In certain embodiments, a conductor may be a part of electrochemical or other type of electrode-like systems that may be used to inject current into a nerve cell.

In some preferred embodiments, the conductors 108 may be attached to a nerve ending in the proximity of the second side of the housing 100. For example, the conductors 108 which may be connected to the generator mechanism 107 located on the first side of the housing 100 may be attached to the nerve ending attached to the second side of the housing 100.

The conductors 108 which may be connected to the cathode terminal and the conductors 108 which may be connected to the anode terminal may create a voltage difference at the place of their attachment to the nerve ending. Such voltage difference may cause depolarization at the nerve ending and may provoke an action potential which may have same, similar, or different properties as the action potential arrived to the opposite side of said device.

For example, it may be assumed that Sodium ions enter a nerve cell during action potential at a rate of 200 ions per a sec, that there may be 1000 voltage gated channels per square micron of a membrane, and that the time of a single depolarizing event may be $1 \times 10^{-3}$ seconds. For a segment of about 5 µm long and 20 µm wide, the surface area may be approximately 314 µm$^2$ [$2 \times \pi \times 10$ µm$\times 5$ µm] which may suggest the presence of approximately 314,000 voltage gated channels. Based on the suggested number of channels, a single depolarizing effect may result in a combine charge of about $1.0048 \times 10^{-11}$ C [$314,000 \times 200 \times 1.6 \times 10^{-19}$ C], where C stands for Coulomb. The resulting charge may exert a force on the rotating mechanism 105 of approximately 0.907 N [$1 \times (4 \times \pi \times \epsilon_0)^{-1} \times q_1 \times q_2 \times r^{-2}$]. The application of such force on the rotating mechanism 105 may create a torque of 11.34 Nµm [T=r×F], where T stands for torque, r stands for radius, and F stands for force. If it may be assumed that the rotating system weights about 350 µg, then the rotating system of such weight may have a moment of inertia of about 0.05 46875 µgµm [$0.5 \times$weight$\times r^2$]. Such torque and such inertia may results in an angular acceleration of 207.36 rad/s$^2$ [torque/inertia]. If it may be assumed that the rotating mechanism 105 may consists of four solenoids with 20 copper coils per solenoid and two magnets that may have a field strength of 0.01 Tesla per magnet; then, the rotation of the rotating mechanism 105 may result in generator an absolute voltage of approximately 800 mV [$-(4 \times 20) \times 0.01$ Tesla/1 s]. Based on widely accepted understanding of characteristics of an action potential, the generated by the device voltage may be sufficient to provoke an active potential.

The method of reviving and maintaining a severed nerve tissue or a bundle of nerves of a body may comprise the steps of: providing a housing 100 for conducting and modulating neural response, the housing having a first end 115, a second end 116 and a cavity, wherein the cavity is interposed between the first end 115 and the second end 116 and the first end 115 of the housing 100 has a plurality of openings and 116 second end of the housing 100 has a plurality of openings; providing at least one conductor 108 in communication with at least one of the first end 115 and the second end 116 for collecting current, wherein each of the conductors 108 are adapted to attach to at least one first nerve ending; and fluids are transported between the first nerve ending and the second nerve ending. The generator mechanism 107 may be inside (or outside) the cavity and triggers a generator event. The generator event may be an acoustic signal, an acoustic wavelength, electric current, a chemical change, an acoustic signal. There may also be at least one sensing mechanism, wherein the sensing mechanism senses a change in nerve and effects a change according to the nerve change. The nerve change may be a change in polarity, current, signal, acoustic, electric, light frequency, photonics, chemical, physical, thermal change and change in chemical concentration. The term "neural response" may be a change of polarity of a nerve (the nerve excites itself as a fuse, the neural impulse is a wave of ions). A neural response may also be the neural impulse traveling from the end of the nerve back to the brain. If the nerve innervates and contracts a muscle, it may be said to have affected the movement of the muscle tissue. The step of transporting fluids may be through at least one pathway and the fluids may be intracellular. The fluids according to the present invention may be any bodily fluids including intracellular, interferon, stem cells and plasma. The fluids may also be stored in a reservoir and may be pumped by a pumping mechanism. The term pathway is intended to include any path in which fluids, electric, acoustic, or chemical signals may travel. The pathway may, but is not limited to, include tubes, microtubes, microfluid channels or any other path.

In summary, the device of FIG. 1 may conduct and modulate nerve signals from a primary end of severed nerve 109 to a secondary end of the severed nerve 110 wherein the first end 115 of the device is connected to a primary end of a severed nerve 109 and the second end 116 of the housing 100 is connected to a secondary end of a severed nerve 110. The first end 115 of the device 100 has a plurality of openings (e.g. 103, 104) which may be of the same of varied sizes and shapes. There is also a rotating mechanism 105 positioned with a cavity of the housing 100, which rotates within the cavity. A generator mechanism 107 is positioned within the cavity and connected to the rotating mechanism 105, and generates electric current upon rotation of the rotating mechanism 105. Conductors 108 collect current from the generator mechanism 107. As such neural signals are conducted between nerve cells.

In some preferred embodiments and methods of operation, the device made in accordance with the invention FIG. 1 may still incorporate various micro-electromechanical systems 120 (MEMS), such as a central processing unit (CPU), memory storage, a sensor, a modifier, or an integrated circuit. In some embodiments, some or all of these micro-electromechanical systems may be attached to walls of the cavity of the housing 100 or may be attached to any part of the rotating mechanism 105, generator mechanism 107, or microfluid channels. In certain embodiments, there may be at least one CPU which may be in electronic communication with at least one memory storage system which may allow CPU to perform more complex functions. Other embodiments may have at least one sensor MEMS device for measuring nerve signals by sensing the substantiality of changes occurring in different parts of the device. The sensor may be in communication with CPU or with the electronic memory storage system. Still other embodiments may have at least one modifier for modifying the device response to nerve signals sensed by the sensor. Still further embodiments, may have at least one electronic integrated circuit which may link all MEMS devices with each other.

The sensor may be in communication with and sample the characteristics of the rotating mechanism 105 of the device (or many rotating mechanisms). In certain embodiments, the sensor may sample the generated current in the generator mechanism 107.

The modifier may adjust the characteristics of the rotating mechanism 105. In some preferred embodiments, the modifier may adjust the characteristics of current produced by the generator mechanism 107.

In some preferred embodiments, the sensor may sample the rotation characteristics of said rotating mechanism 105. The sampled information may be analyzed, may be stored, or may be used to adjust the rotation characteristics of the rotating mechanism 105 which may bring about the generator mechanism 107 to adjust the generated current which may be transmitted along the conductors 108 to initiate an action potential in a nerve ending. In other preferred embodiments, in which the sensor may sample the characteristics of the current, the sampled information may be analyzed, may be stored, or may be directly communicated to the modifier to adjust the characteristics of the current which the generator mechanism 107 may transmit along the conductors 108 to initiate an action potential in a nerve ending.

Figure 2:
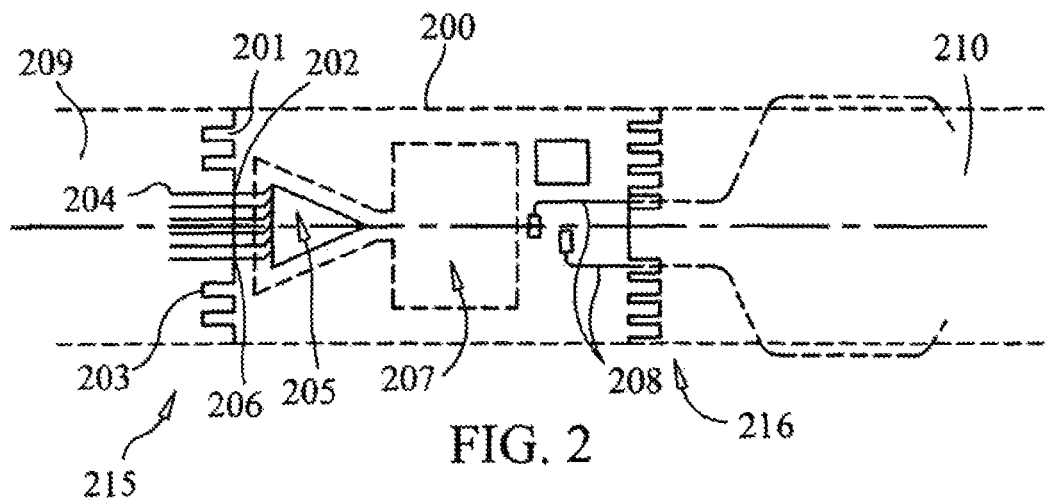
FIG. 2 is a diagram according to one aspect of the present invention.

In some preferred embodiments and methods of operation, the neural bridge device made in accordance with the invention, FIG. 2, may incorporate a housing 200 having a first end 215, a second end and a cavity. The diameter of the housing may vary from approximately 1 μm to approximately 1 cm, depending on the type of nerve cells in which said device may be implanted. The length of the device may vary depending on the extensiveness of a particular medical condition. In some embodiments, the length of the device varies from approximately 2 μm to approximately 1 cm. In some other embodiments, the housing may be made from any electrostatic plastic material such as cellophane or more rigorous like a diamond.

The first and second ends of said the housing may have at least two types of openings. In some embodiments, there are at least two openings of each type. In some other embodiments, the openings on the first end of the housing may be of the same size and shape, and the openings on the second end of the housing may be of the same size and shape.

In some preferred embodiments, the openings may vary in diameter. The openings of first type 201 may have a larger diameter than the openings of the second type 202. In still other embodiments, the openings of the second type may be present only on first end 215 of the housing. The openings of the first type may have a larger diameter and may serve for movement of cell material through the device which may permit to restore the anterograde and retrograde exchange of cell material between the severed parts of a nerve.

The openings of the first type on the first end 215 of the housing and the opening of the first type on the second end 216 of the housing 200 may merge or may be connected to hollow tubular extensions 203 which may have the same diameter as the diameter of the openings of the first type. In some preferred embodiments, the openings of the first type on the first end 215 of the housing 200 may be connected with the opening of the first type located on the second side of the housing by a connective tube or a cavity of some other shape. Such unity of hollow tubular extension 203 and the opening of the first type of the first end 215 of the housing 200 with a connective tube and the opening of the first type of the second end 216 of the housing 200 may create a single cavity, which may be called a microfluid channel. In some embodiments, the microfluid channel may be made as a single form having a hollow inside, for example it may be in a form of a tube, which may go through entire device. The length of the microfluid channel may vary from approximately 1 μm to approximately 5 cm. The microfluid channel may allow for unimpeded traveling of cell material from the first end 215 of the severed axon to the second end 216 of the severed axon.

The openings of the second type on the first end 215 of the housing may have a smaller diameter and may serve to direct ions such as sodium ions to enter the cavity of the housing. The ions may enter a nerve cell at increased numbers during the depolarization stage of an action potential. The openings of the second type may merge or may be connected to some hollow tubular extension 204, for example it may be a tube. A unity at the opening of the second type and the hollow tubular extension 204 may be called an ion-guiding channel. In some embodiments, the ion-guiding channel may have the same diameter as the diameter of the openings of the second type.

The invention may further incorporate at least one rotating mechanism 205 positioned within the cavity of the housing. The rotating mechanism 205 may rotate within the cavity and along a longitudinal axis of the housing. The rotating mechanism 205 may be a turbine, shaped like a cone, positioned such that the sharpest end may look inside the housing. The rotating mechanism 205 may have needle-like protrusions 206 which may be referred to as micro-terminals. The micro-terminals may carry an electric charge. The micro-terminals may be positioned to face the second type openings, or ion-guiding channels on the first end 215 of the housing 200.

The needle-like protrusions 206, or micro-terminals, may be set at an angle of approximately thirty to approximately sixty degrees relatively to the plane of the ion-guiding channels linked to the openings of the second type. In some preferred embodiments, the micro-terminals may be positioned at approximately forty-five degrees relatively to the plane of the ion-guiding channels linked to the openings of the second type (e.g. 204). The needle-like protrusions 206, or micro-terminals, may have the same charge as the ions entering the housing through the ion-guiding channels.

In some preferred embodiments, the micro-terminals may carry positive charge. During an action potential, sodium ions, which may enter the cell during the depolarization stage of the action potential, may be directed by the ion-guiding channels toward the micro-terminals of the rotating mechanism. Since sodium ions and the micro-terminals have the same charge, the micro-terminals may be repelled away from the ion-guiding channels. The process of repulsion may displace the rotating mechanism 205 and bring about the rotation of the rotating mechanism 205.

The invention may further incorporate at least one generator mechanism 207 positioned within the cavity of the housing 200 and connected to the rotating mechanism 205. For example, when rotating mechanism 205 may have shape of a cone, the generator mechanism 205 may be connected to the sharpest end. In some preferred embodiments, the generator mechanism 205 may represent a cluster of conducting wires rotating between the poles of a magnet or an electromechanical motor such as a dynamo.

The displacement of the rotating mechanism 205 upon influx, or entry, of sodium ions through the ion-guiding channels linked to the openings of the second type may result in the rotation of the rotating mechanism 205 which may result in a movement of some part of the generator mechanism 207 along a longitudinal axis of the housing such as conducting wires around a magnet if the generator mechanism 207 may consist of conducting wires and a magnet or a rotor in an electromechanical motor if the generator mechanism 207 may consist of an electromotor.

The rotation of a part of the generator mechanism 207 such as conducting wires or rotor may result in changes in magnetic field within the generator mechanism 207. In accordance with the Faraday laws, these changes may produce current within the generator mechanism 207, for example in conducting wires or in a stator of an electromechanical motor. In some embodiments, the generator mechanism 207 may produce electric potential from at least approximately 7 mV to approximately 60 mV.

The invention may further incorporate a plurality of conductors 208 for collecting and moving current from the generator mechanism 207. In some embodiments, there may be at least two conductors 208. Some of the conductors 208 may be connected to the cathode terminals of the generator mechanism 207 and some of said conductors may be connected to the anode terminals of the generator mechanism 207.

A single conductor may be a piece of a wire from any conducting material such as copper. In some other preferred embodiments, the conductors may be made out of polyacytelene. In some still other preferred embodiments, the conductors may be made in a shape of a tube of micro- or nano size. In certain embodiments, a conductor may be a part of electrochemical or other type of electrode-like systems that may be used to inject current into a nerve cell.

In some preferred embodiments, the conductors may be attached to a nerve ending in the proximity of the second side of the housing. For example, the conductors which may be connected to the generator mechanism located on the first side of the housing may be attached to the nerve ending attached to the second side of the housing.

The conductors which may be connected to the cathode terminal and the conductors which may be connected to the anode terminal may create a voltage difference at the place of their attachment to the nerve ending. Such voltage difference may cause depolarization at the nerve ending and may provoke an action potential which may have same, similar, or different properties as the action potential arrived to the opposite side of said device.

In summary, the device of FIG. 2 may conduct and modulate nerve signals from a primary end of severed nerve 209 to a secondary end of the severed nerve 210 wherein the first end 215 to the device is connected to the primary end of a severed nerve 209 and the second end of the housing is connected to a secondary end of a severed nerve 210.

In some preferred embodiments and methods of operation, the device made in accordance with the invention FIG. 2 may still incorporate various micro-electromechanical systems (MEMS), such as a central processing unit (CPU), memory storage, a sensor, a modifier, or an integrated circuit. The MEMS may be inside the device or outside the device. It may also be partially contained within the human body, such as an intravenous connection. In some embodiments, some or all of these micro-electromechanical systems may be attached to walls of the cavity of the housing or may be attached to any part of the rotating mechanism, generator mechanism, or microfluid channels. In certain embodiments, there may be at least one CPU which may be in electronic communication with at least one memory storage system which may allow CPU to perform more complex functions. Other embodiments may have at least one sensor MEMS device for measuring nerve signals by sensing the substantiality of changes occurring in different parts of the device. The sensor may be in communication with CPU or with the electronic memory storage system. Still other embodiments may have at least one modifier for modifying the device response to nerve signals sensed by the sensor. Still further embodiments, may have at least one electronic integrated circuit which may link all MEMS devices with each other.

The sensor may sample the characteristics of the rotating mechanism of the device. In certain embodiments, the sensor may sample the generated current in the generator mechanism.

The modifier may adjust the characteristics of the rotating mechanism. In some preferred embodiments, the modifier may adjust the characteristics of current produced by the generator mechanism.

In some preferred embodiments, the sensor may sample the rotation characteristics of the rotating mechanism. The sampled information may be analyzed, may be stored, or may be used to adjust the rotation characteristics of the rotating mechanism which may bring about the generator mechanism to adjust the generated current which may be transmitted along the conductors to initiate an action potential in a nerve ending. In other preferred embodiments, in which the sensor may sample the characteristics of the current, the sampled information may be analyzed, may be stored, or may be directly communicated to the modifier to adjust the characteristics of the current which the generator mechanism may transmit along the conductors to initiate an action potential in a nerve ending.

Figure 3:
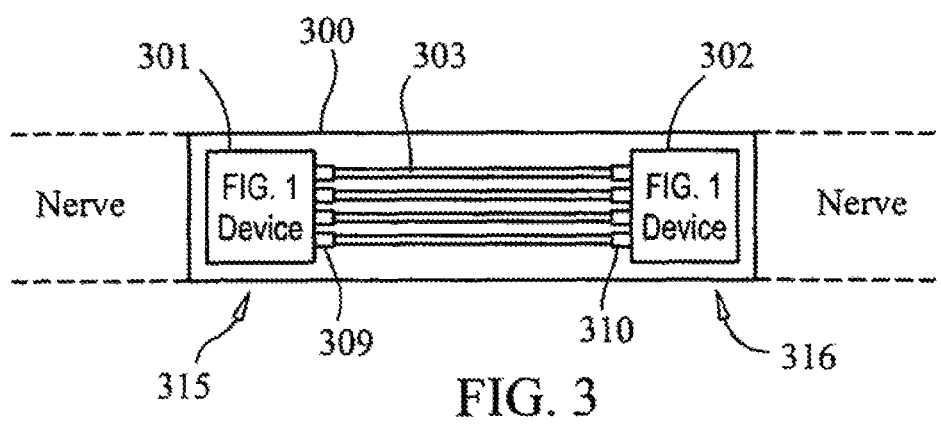
FIG. 3 is a diagram according to one aspect of the present invention.

In some preferred embodiments and methods of operation, the neural bridge device made in accordance with the invention, FIG. 3, may incorporate a housing 300 having a first end 315, a second end 316 and a cavity. There may be a first device 301 (such as that depicted in FIG. 1) located in the first end 315 of the housing 300; and there may be a second device 302 (such as that depicted in FIG. 1) located in the second end 316 of the housing 300. It is envisioned that the term device is interchangeable with the term neural bridge device and is intended to denote many different embodiments as depicted in the figures and disclosed herein.

In some preferred embodiments, the first device 301 may be positioned having its first side of its housing 300, which may carry the ion-guiding channels, looking at the primary end of a severed nerve 309. In addition, the second device 302 may be positioned having its first side of its housing 300, which may carry the ion-guiding channels, looking at the secondary end of a severed nerve 310.

In certain embodiments, at least one hollow tubular extension on the second end of the first device 301 may be linked to at least one hollow tubular extension (e.g. 103) on the first end of the second device 302 through hollow tubular extensions 303 having a cavity. In some other certain embodiments, the hollow tubular extensions 303 may connect at least one microfluid channel of the first device 301 with at least one microfluid channel of the second device 302. In some preferred embodiments, the hollow tubular extensions 303 may have a length from approximately 1 μm to approximately 5 cm. In some other preferred embodiments, the form may be shaped as a tube and may be referenced as a microtube. The microtube may allow for unimpeded traveling of cell material from the first end of the severed axon to the second end of the severed axon. In still other preferred embodiments, the microtube may be composed of any plastic material.

The device made in accordance with the invention FIG. 3 may still incorporate various micro-electromechanical systems (MEMS), such as a central processing unit (CPU), memory storage, a sensor, a modifier, or an integrated circuit. In some preferred embodiments, the first device 301 on the first side 315 of the housing 300 and the second device 302 on the second side 316 of the housing 300 may share the various micro-electromechanical systems. In still other preferred embodiments, the first device 301 on the first side of the housing 300 may have its own set of various micro-electromechanical systems, and the second device 302 on the second side of the housing 300 may have its own set of various micro-electromechanical systems. Some or all of these micro-electromechanical systems may be attached to walls of the cavity of the housing 300 or may be attached to any part of the first device 301, the second device 302, and or to microtubes 303. There may be at least one CPU which may be in electronic communication with at least one memory storage system which may allow the CPU to perform more complex functions. There may be at least one sensor MEMS device for measuring nerve signals by sensing the substantiality of changes occurring in different parts of the device. The sensor may be in communication with CPU or with the electronic memory storage system. Still other embodiments may have at least one modifier for modifying the device response to nerve signals sensed by the sensor. There may be at least one electronic integrated circuit which may link all MEMS devices with each other.

The sensor may sample the characteristics of the rotating mechanism located in the first device and the second device. The sensor may sample generated current at the generator mechanism of the first device and at the generator mechanism of the second device.

The modifier may adjust the characteristics of rotating mechanism in the first device or the second device. In some preferred embodiments, the modifier may adjust the characteristics of generated current produced by the generator mechanism located in the first device or in the second device.

The sensor may sample the rotation characteristics of the rotating mechanism. The sampled information may be analyzed, stored, or used to adjust the rotation characteristics of the rotating mechanism, in the first device or the second device, which may bring about the generator mechanism, in the first device 301 or in the second device 302, to adjust the generated current which may be transmitted along the conductors to initiate an action potential in a nerve ending. The sensor may sample the characteristics of the current, the sampled information may be analyzed, stored, or may be directly communicated to the modifier to adjust the characteristics of the current which the generator mechanism, in the first device or in the second device, may transmit along the conductors to initiate an action potential in a nerve ending.

Figure 4:
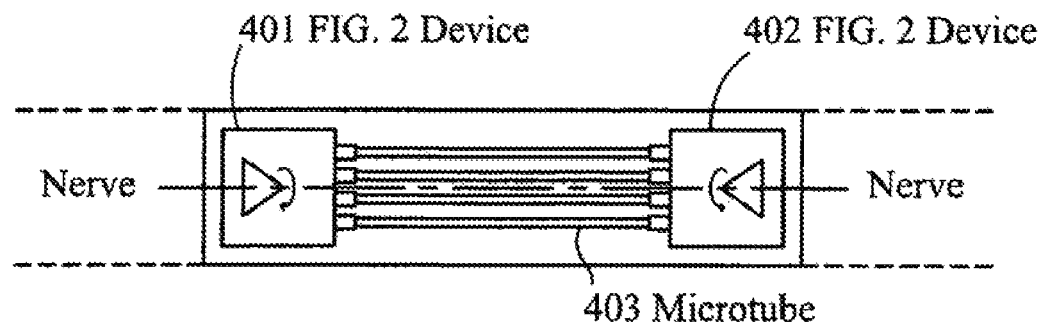
FIG. 4 is a diagram according to one aspect of the present invention.

The neural bridge device, as depicted in FIG. 4, may incorporate a housing 400 having a first end, a second end and a cavity. There may be a first device 401 of FIG. 2 located in the first end of the housing 400; and there may be a second device 402 of FIG. 2 located in the second end of the housing 400.

In some preferred embodiments, the first device 401 may be positioned having its first side of its housing 400, which may carry the ion-guiding channels, facing the first end of a severed nerve. In addition, the second device 402 may be positioned having its first side of its housing 400, which may carry the ion-guiding channels, facing the second end of a severed nerve.

In certain embodiments, at least one hollow tubular extension on the second end of the first device 401 may be linked to at least one hollow tubular extension on the first end of the second device 402 through a hollow form 403 having a cavity. In some other certain embodiments, the form 403 may connect at least one microfluid channel of the first device 401 with at least one microfluid channel of the second device 402. In some preferred embodiments, the form 403 may have a length from approximately 1 μm to approximately 5 cm. In some other preferred embodiments, the form may be shaped as a tube and may be referenced as a microtube. The microtube may allow for unimpeded traveling of cell material from the first end of the severed axon to the second end of the severed axon. In still other preferred embodiments, the microtube may be composed of any plastic material.

In some preferred embodiments and methods of operation, the device made in accordance with the invention FIG. 4 may still incorporate various micro-electromechanical systems (MEMS), such as a central processing unit (CPU), memory storage, a sensor, a modifier, or an integrated circuit. In some preferred embodiments, the first device 401 on the first side of the housing 400 and the second device 402 on the second side of the housing 400 may share the various micro-electromechanical systems. In still other preferred embodiments, the first device 401 on the first side of the housing 400 may have its own set of various micro-electromechanical systems, and the second device 402 on the second side of the housing 400 may have its own set of various micro-electromechanical systems. Some or all of these micro-electromechanical systems may be attached to walls of the cavity of the housing 400 or may be attached to any part of the first device 401, the second device 402, and or to microtubes 403. In certain embodiments, there may be at least one CPU which may be in electronic communication with at least one memory storage system which may allow CPU to perform more complex functions. Other embodiments may have at least one sensor MEMS device for measuring nerve signals by sensing the substantiality of changes occurring in different parts of the device. The sensor may be in communication with CPU or with the electronic memory storage system. There may be at least one modifier for modifying the device response to nerve signals sensed by the sensor. Still further embodiments, may have at least one electronic integrated circuit which may link all MEMS devices with each other.

The sensor may sample the characteristics of the rotating mechanism located in the first device and the second device. In certain embodiments, the sensor 405 may sample generated current at the generator mechanism of the first device and at the generator mechanism of the second device.

The modifier may adjust the characteristics of rotating mechanism in the first device or the second device. In some preferred embodiments, the modifier may adjust the characteristics of generated current produced by the generator mechanism located in the first device or in the second device.

In some preferred embodiments, the sensor may sample the rotation characteristics of said rotating mechanism. The sampled information may be analyzed, may be stored, or may be used to adjust the rotation characteristics of the rotating mechanism, in the first device or in the second device, which may bring about the generator mechanism, in the first device or in the second device, to adjust the generated current which may be transmitted along the conductors to initiate an action potential in a nerve ending. In still other preferred embodiments, in which the sensor may sample the characteristics of the current, the sampled information may be analyzed, may be stored, or may be directly communicated to the modifier to adjust the characteristics of the current which the generator mechanism, in the first device or in the second device, may transmit along the conductors to initiate an action potential in a nerve ending.

Figure 5:
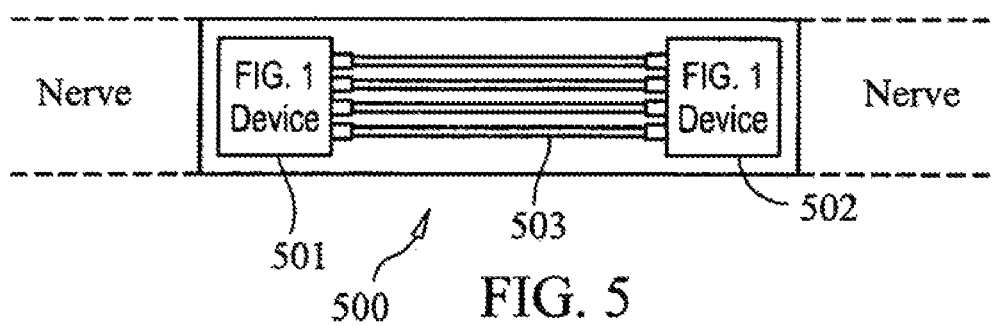
FIG. 5 is a diagram according to one aspect of the present invention.

In some preferred embodiments and methods of operation, the neural bridge device made in accordance with the invention, FIG. 5, may consist of a first device 501 of FIG. 1 which may be positioned in the first nerve ending and a second device 502 of FIG. 1 which may be positioned in the second nerve ending. In some further preferred embodiments, there may be at least one microtube 503 connecting at least one hollow tubular extension on the second end of the first device 501 with at least one extension on the second end of the second device 502. In certain other preferred embodiments, the microtube may be composed of any plastic material.

In some preferred embodiments, the first device 501 may be positioned having its first side of its housing 500, which may carry the ion-guiding channels, facing the first end of a severed nerve. In addition, the second device 502 may be positioned having its first side of its housing 400, which may carry the ion-guiding channels, facing the second end of a severed nerve.

Figure 6:
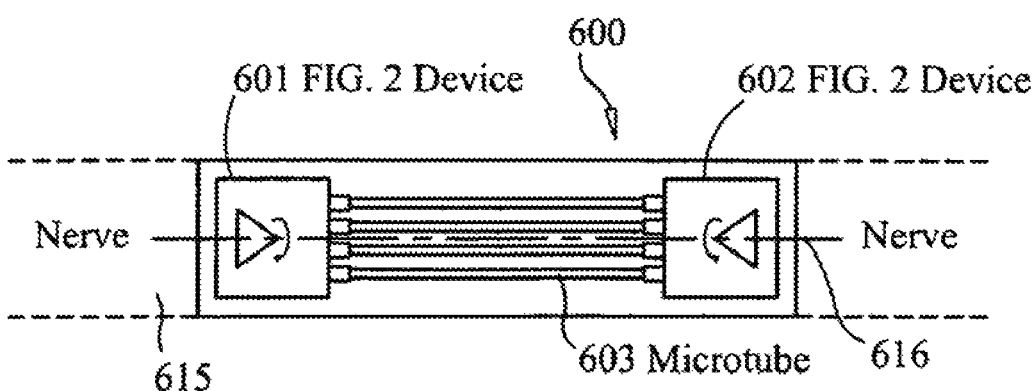
FIG. 6 is a diagram according to one aspect of the present invention.

In some preferred embodiments and methods of operation, the neural bridge device made in accordance with the invention, FIG. 6, may consist of a first device 601 of FIG. 2 which may be positioned in the first nerve ending and a second device 602 of FIG. 2 which may be positioned in the second nerve ending. In some further preferred embodiments, there may be at least one microtube 603 connecting at least one hollow tubular extension on the second end of the first device 601 with at least one extension on the second end of the second device 602. In certain other preferred embodiments, the microtube may be composed of any plastic material.

In some preferred embodiments, the first device 601 may be positioned having its first side of its housing 600, which may carry the ion-guiding channels, facing the first end of a severed nerve. In addition, the second device 602 may be positioned having its first side 615 of its housing 600, which may carry the ion-guiding channels, facing the second end of a severed nerve.

The invention may further incorporate a method for modulating nerve signals. According to some embodiments of the invention, the device of FIG. 1 carrying some or all of the MEMS devices which may be associated with certain embodiments of the device of FIG. 1 may be secured between the first end of a severed nerve and the second end of a severed nerve. The desired signals may be communicated to the device by any suitable means. The device may modify receiving nerve signal in accordance with the desired signals which may have been communicated to the device. In some embodiments, the device may communicate the signals away from the device by any suitable means.

According to some embodiments of the invention, there may be at least two devices of FIG. 1 secured between the first end of a severed nerve and the second end of the severed nerve, the desired signals may be communicated to the devices by any suitable means, and the devices may modify receiving nerve signal in accordance with the desired signals which may have been communicated to said devices. In some embodiments, the devices may communicate the signals away from the devices by any suitable means. In some other embodiments, the devices may communicate the desired signals among each other in synchronous or asynchronous manner. In some other embodiments, the devices may modify nerve responses outside a particular nerve cell containing one or many devices of FIG. 1. In still other preferred embodiments, there may be a centralized controlling device implanted which may control the functionality of the devices of FIG. 1.

The invention may further incorporate a method for modulating nerve signals. According to some embodiments of the invention, the device of FIG. 2 carrying some or all of the MEMS devices which may be associated with certain embodiments of the device of FIG. 2 may be secured between the first end of a severed nerve and the second end of a severed nerve. The desired signals may be communicated to the device by any suitable means. The device may modify receiving nerve signal in accordance with the desired signals which may have been communicated to the device. In some embodiments, the device may communicate the signals away from the device by any suitable means. The term neural bridge device is intended to include any of the various neural devices disclosed herein interchangeably without limitation.

According to some embodiments of the invention, there may be at least two devices of FIG. 2 secured between the first end of a severed nerve and the second end of the severed nerve, the desired signals may be communicated to the devices by any suitable means, and the devices may modify receiving nerve signal in accordance with the desired signals which may have been communicated to said devices. In some embodiments, the devices may communicate the signals away from the devices by any suitable means. In some other embodiments, the devices may communicate the desired signals among each other in synchronous or asynchronous manner. In some other embodiments, the devices may modify nerve responses outside a particular nerve cell containing one or many devices of FIG. 2. In still other preferred embodiments, there may be a centralized controlling device implanted which may control the functionality of the devices of FIG. 2.

The invention may further incorporate a method for modulating nerve signals. According to some embodiments of the invention, the device of FIG. 3 carrying some or all of the MEMS devices which may be associated with certain embodiments of the device of FIG. 3 may be secured between the first end of a severed nerve and the second end of a severed nerve. The desired signals may be communicated to the device by any suitable means. The device may modify receiving nerve signal in accordance with the desired signals which may have been communicated to the device. In some embodiments, the device may communicate the signals away from the device by any suitable means.

According to some embodiments of the invention, there may be at least several devices of FIG. 3 implanted into a human body, the desired signals may be communicated to the devices by any suitable means, and the devices may modify receiving nerve signal in accordance with the desired signals which may have been communicated to said devices. In some embodiments, the devices may communicate the signals away from the devices by any suitable means. In some other embodiments, the devices may communicate the desired signals among each other in synchronous or asynchronous manner. In some other embodiments, the devices may modify nerve responses outside a particular nerve cell containing one or many devices of FIG. 3. In still other preferred embodiments, there may be a centralized controlling device implanted which may control the functionality of the devices of FIG. 3.

The invention may incorporate a method for modulating nerve signals. According to some embodiments of the invention, the device of FIG. 4 carrying some or all of the MEMS devices which may be associated with certain embodiments of the device of FIG. 4 may be secured between the first end of a severed nerve and the second end of a severed nerve. The desired signals may be communicated to the device by any suitable means. The device may modify receiving nerve signal in accordance with the desired signals which may have been communicated to the device. In some embodiments, the device may communicate the signals away from the device by any suitable means.

There may several devices as depicted in FIG. 4 implanted into a human body and the desired signals may be communicated to the devices by any suitable means. The devices may modify receiving nerve signal in accordance with the desired signals which may have been communicated to said devices. In some embodiments, the devices may communicate the signals away from the devices by any suitable means. In some other embodiments, the devices may communicate the desired signals among each other in synchronous or asynchronous manner. In some other embodiments, the devices may modify nerve responses outside a particular nerve cell containing one or many devices of FIG. 4. In still other preferred embodiments, there may be a centralized controlling device implanted which may control the functionality of the devices of FIG. 4.

The invention may further incorporate a method for modulating nerve signals. According to some embodiments of the invention, the device of FIG. 5 carrying some or all of the MEMS devices which may be associated with certain embodiments of the device of FIG. 5 may be secured between the first end of a severed nerve and the second end of a severed nerve. The desired signals may be communicated to the device by any suitable means. The device may modify receiving nerve signal in accordance with the desired signals which may have been communicated to the device. In some embodiments, the device may communicate the signals away from the device by any suitable means.

According to some embodiments of the invention, there may be at least several devices of FIG. 5 implanted into a human body, the desired signals may be communicated to the devices by any suitable means, and the devices may modify receiving nerve signal in accordance with the desired signals which may have been communicated to said devices. In some embodiments, the devices may communicate the signals away from the devices by any suitable means. In some other embodiments, the devices may communicate the desired signals among each other in synchronous or asynchronous manner. In some other embodiments, the devices may modify nerve responses outside a particular nerve cell containing one or many devices of FIG. 5. In still other preferred embodiments, there may be a centralized controlling device implanted which may control the functionality of the devices of FIG. 5.

According to one embodiment of the present invention, the device 600 as depicted in FIG. 6, may carry some or all of the MEMS devices. The device 600 may be secured between the primary end of a severed nerve 615 and the secondary end of a severed nerve 616. The desired signals may be communicated to the device 600 by any suitable means. The device 600 may receive and modify nerve signals in accordance with the desired signals which may have been communicated to the device. The device 600 may communicate the signals away from the device by any suitable means.

There may be several devices implanted into a human body, the desired signals may be communicated to the devices by any suitable means, and the devices may modify receiving nerve signal in accordance with the desired signals which may have been communicated to said devices. In some embodiments, the devices may communicate the signals away from the devices by any suitable means. In some other embodiments, the devices may communicate the desired signals among each other in synchronous or asynchronous manner. In some other embodiments, the devices may modify nerve responses outside a particular nerve cell containing one or many devices of FIG. 6. In still other preferred embodiments, there may be a centralized controlling device implanted which may control the functionality of the devices of FIG. 6.

Figure 7:
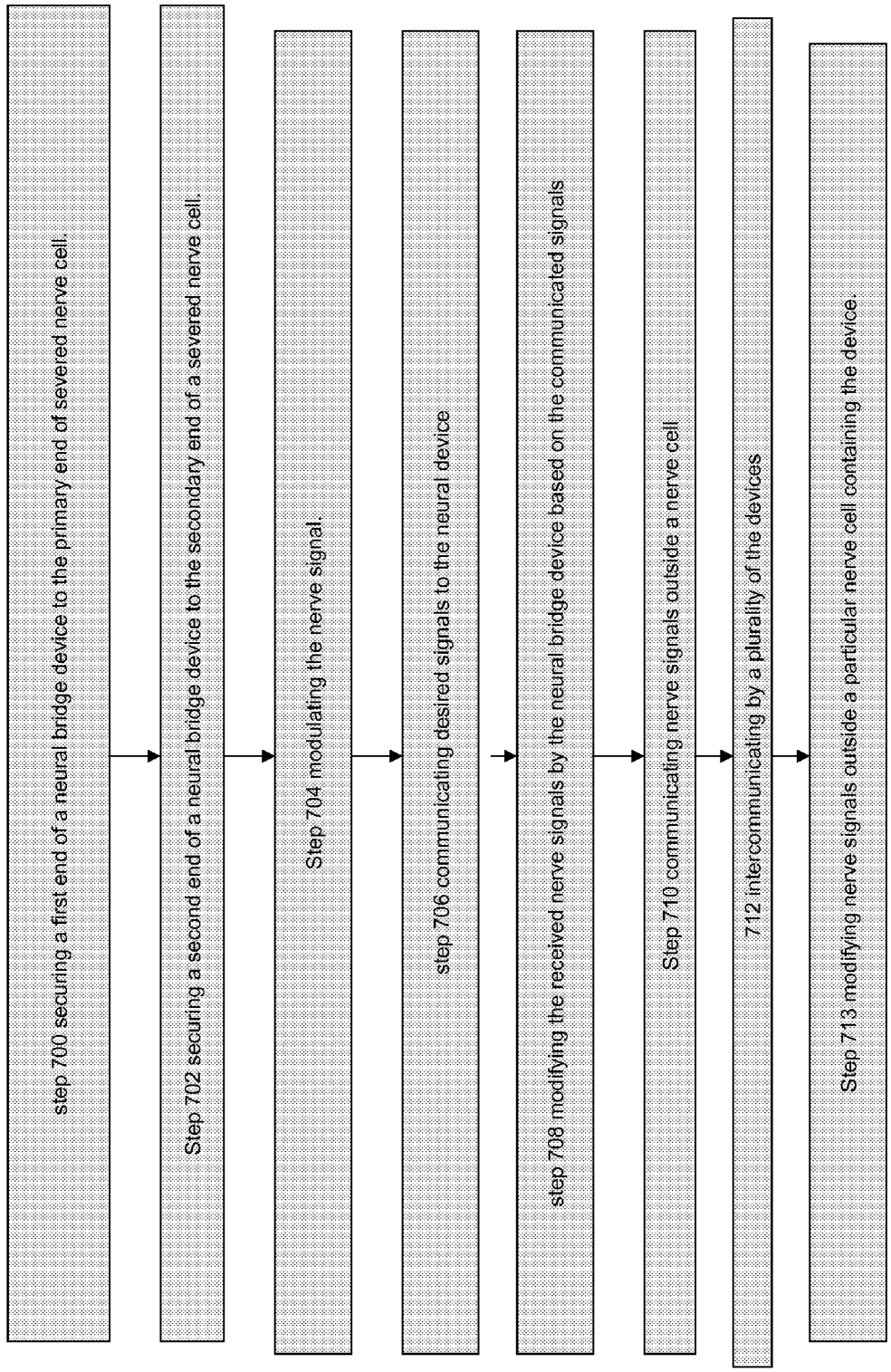
FIG. 7 is a diagram according to one aspect of the present invention.
Figure 8:
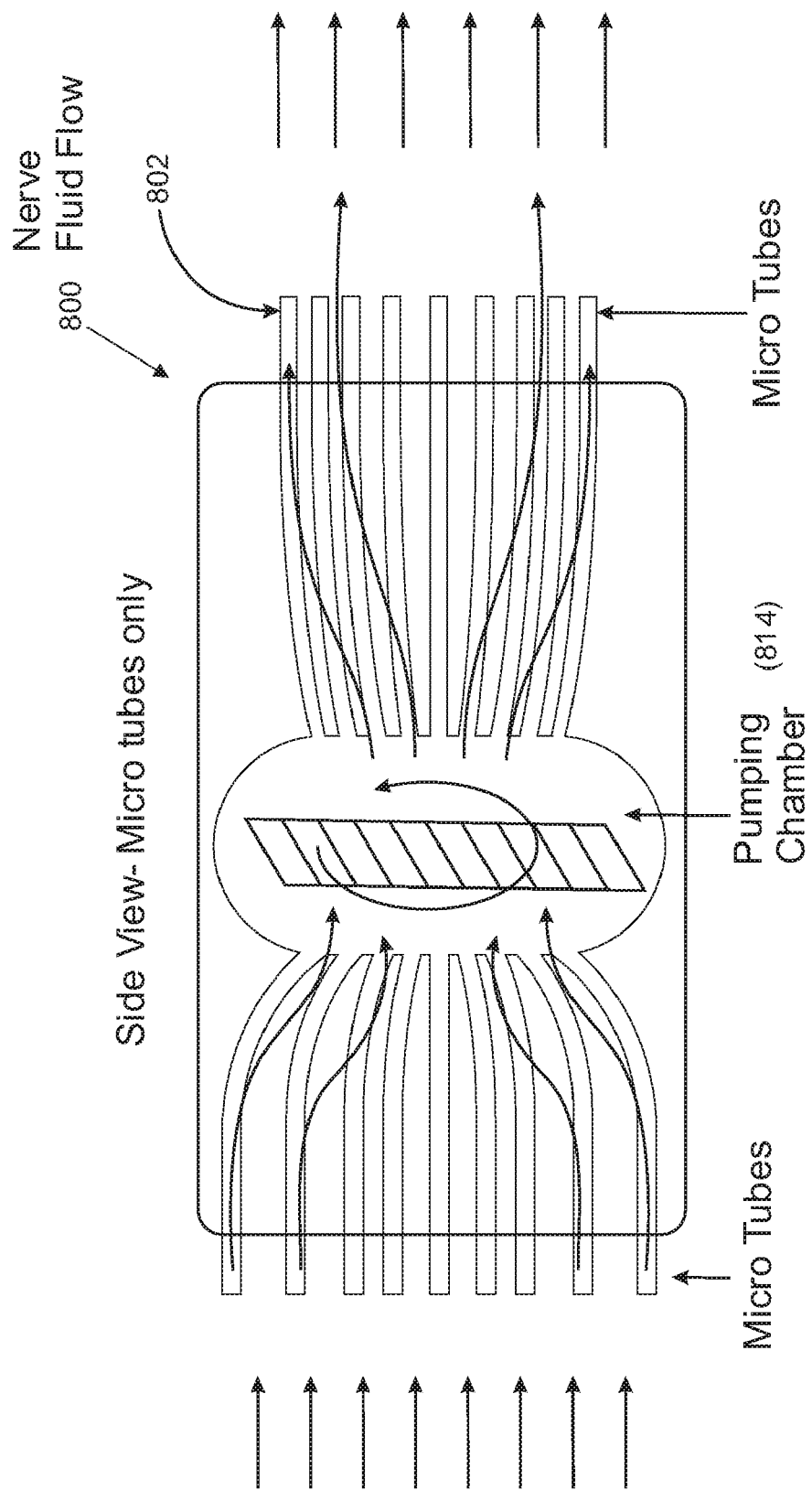
FIG. 8 is a diagram according to one aspect of the present invention.
Figure 9:
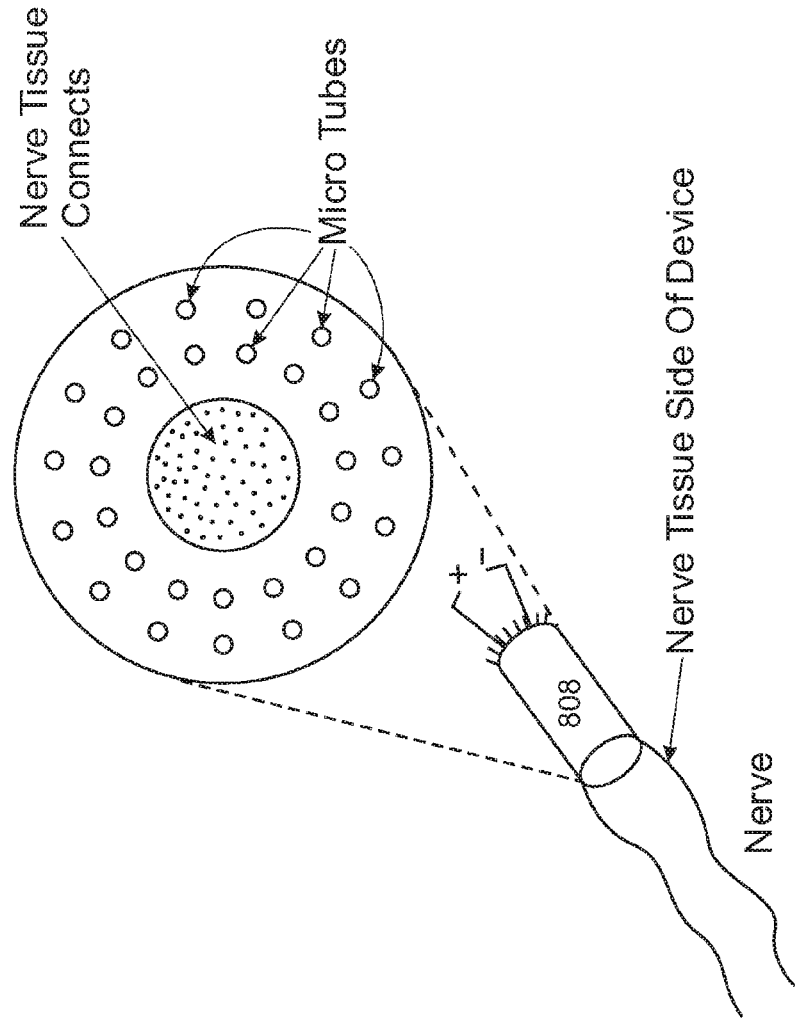
FIG. 9 is a diagram according to one aspect of the present invention.
Figure 10:
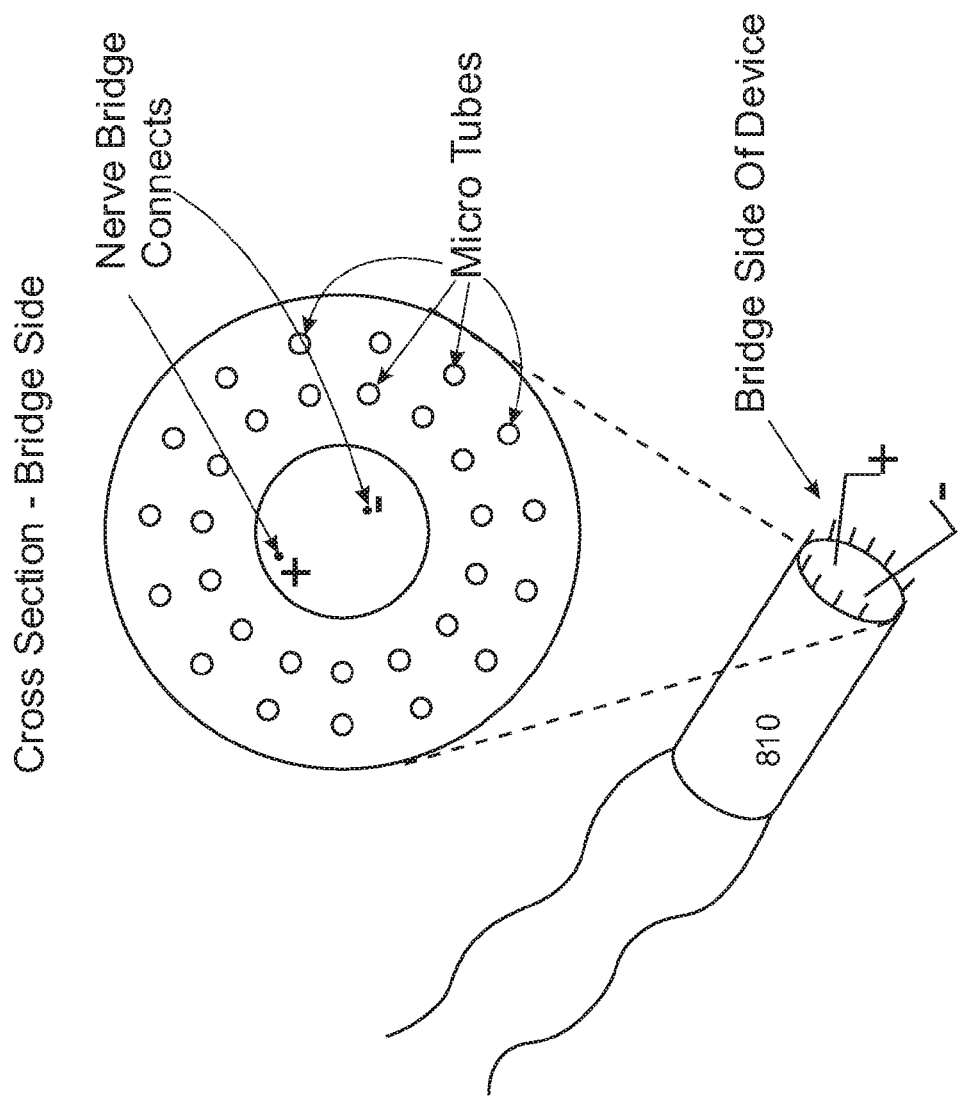
FIG. 10 is a diagram according to one aspect of the present invention.

FIG. 7 depicts a method of restoring nerve signals, according to a preferred embodiment. The method may comprise the steps of: step 700 securing a first end of a neural bridge device to the primary end of severed nerve cell. The term neural bridge is intended to include all variants of the present invention devices. Step 702 securing a second end of a neural bridge device to the secondary end of a severed nerve cell. Step 704 may be modulating the nerve signal. Modulating a nerve signal may further comprise the steps of: step 706 communicating desired signals to the neural device, and step 708 modifying the received nerve signals by the neural bridge device based on the communicated signals. Step 710 may be communicating nerve signals outside a nerve cell. Step 712 may be intercommunicating by a plurality of the devices. Step 713 modifying nerve signals outside a particular nerve cell containing the device. The term maintaining includes sustaining, re-enabling, re-innervating, and maintaining the nerve.

As shown in FIG. 8-11, the housing 800 may contain pathways such as microtubes for transporting fluids from a first end 804 to a second end 806. According to the example shown, there are two conductors 808 and 810. The first conductor 808 is in communication with first end 804 and the second conductor 810 is in communication with the second end 806. As shown the fluids and electric, acoustic, and chemical signals travel between the first nerve ending 804 and the second nerve ending 806. There may also be a pumping means 814 for pumping the fluids.

It should be understood that the foregoing relates to preferred embodiments of the invention and that modifications may be made without departing from the spirit and scope of the invention as set forth in the following claims.

We claim:

1. A method of reviving and maintaining a severed nerve tissue or a bundle of nerves of a body, the severed nerve tissue having a primary nerve ending, that carries an action potential, and a secondary nerve ending that is disconnected from central nervous system, said method comprising:
    providing a housing for conducting and modulating neural response, said housing having a first end, a second end and a cavity interposed between said first end and said second end, wherein said first end has a plurality of openings and said second end has a plurality of openings;
    providing a plurality of conductors in communication with said first end of said housing, wherein said conductors are adapted to attach to at least one of said primary and secondary nerve endings;
    coupling said first end of said housing to the primary nerve ending;
    providing hollow tubular extensions coupled to said openings on said second end of said housing and extending to openings on a second end of an additional housing;
    coupling a first end of the additional housing to the secondary nerve ending; and
    transporting fluids between said primary nerve ending and said secondary nerve ending,
    wherein said fluids are intracellular and are stored in a reservoir.

2. A method of reviving and maintaining a nerve as in claim 1, further comprising the step of pumping said fluids between the primary nerve ending and the secondary nerve ending.

3. A method of reviving and maintaining a severed nerve cell, the severed nerve cell having a primary nerve ending, that carries an action potential, and a secondary nerve ending, said method comprising:
    providing a device for connecting said primary and secondary nerve endings of severed nerve cells and conducting neural signals, said device comprising:
        a housing for conducting and modulating neural response, said housing having a first end, a second end and a cavity, wherein said cavity is interposed between said first end and said second end, and wherein said first end has a plurality of openings and said second end has a plurality of openings,
        at least one generator mechanism positioned within the cavity for generating a current responsive to the action potential of the primary ending of the severed nerve cell,
        a plurality of conductors coupled to said generator mechanism for collecting current from said generator mechanism, wherein said conductors are adapted to attach to a nerve ending, and
        a plurality of ion-guiding channels connected to said openings on said first end of said housing;
    coupling the primary nerve ending of the severed nerve cell to said first end of said housing;
    coupling the secondary nerve ending of the severed nerve cell to said second end of said housing; and transporting fluids between said primary nerve ending and said secondary nerve ending by pumping said fluids, wherein the generator receives a current related to the action potential from the primary nerve ending, and wherein the conductors conduct a current responsive to the action potential from the generator to the secondary nerve ending.

4. A method as in claim 3, further comprising a rotating mechanism positioned with said cavity of said housing, wherein said rotating mechanism has protrusions set at an angle to said ion guiding channel, wherein said rotating mechanism rotates responsive to the action potential from the primary nerve ending, and wherein said rotating mechanism is coupled to said generator and provides a current responsive to the action potential to the generator.

5. A method as in claim 4, wherein said protrusions have the same charge as ions in said at least one ion guiding channel.

* * * * *